United States Patent [19]

White, Jr.

[11] 4,235,817

[45] Nov. 25, 1980

[54] 2-AMINO-5-CHLORO-N-(2,2-DIMETHOXYE-THYL)BENZAMIDE

[75] Inventor: Ralph L. White, Jr., Norwich, N.Y.

[73] Assignee: Morton-Norwich Products, Inc., Norwich, N.Y.

[21] Appl. No.: 75,996

[22] Filed: Sep. 17, 1979

[51] Int. Cl.$^3$ .................. C07C 103/78; A61K 31/165
[52] U.S. Cl. ..................................... 564/163; 424/324
[58] Field of Search ................................. 260/558 A

[56] References Cited

U.S. PATENT DOCUMENTS

| | | | |
|---|---|---|---|
| 3,351,659 | 11/1967 | Santilli et al. | 260/558 A |
| 3,452,037 | 6/1969 | Santilli et al. | 260/558 A X |
| 4,060,638 | 11/1977 | Anderson | 260/558 A X |

FOREIGN PATENT DOCUMENTS 778372  2/1968  Canada ............................... 260/558 A

OTHER PUBLICATIONS

Santilli et al., CA 71: 81338g (1969).
Santilli et al., CA 68: 114264y (1968).

*Primary Examiner*—Thomas A. Waltz
*Attorney, Agent, or Firm*—Anthony J. Franze

[57] ABSTRACT

2-Amino-5-chloro-N-(2,2-dimethoxyethyl)benzamide is useful as a muscle relaxant.

1 Claim, No Drawings

2-AMINO-5-CHLORO-N-(2,2-DIMETHOXYETHYL)BENZAMIDE

This invention is concerned with the chemical compound 2-amino-5-chloro-N-(2,2-dimethoxyethyl)benzamide.

The compound of this invention is useful as a muscle relaxant when administered to warm-blooded animals. Thus, when administered to rabbits in the commonly employed test for detecting effect upon the flexor reflex, this compound elicits an effect comparable to that exhibited by mephenesin at a dose, intravenously, of about 40 mg/kg in a physiologically acceptable menstruum such as dimethylsulfoxide, tetrahydrofuran or mannitol-aqueous sodium hydroxide solution.

The compound of this invention is readily formulated into pharmaceutical compositions such as tablets, suspensions, solutions, elixirs, capsules and the like using adjuvants and vehicles commonly employed in the pharmaceutical art.

In order that this invention may be readily available to and understood by those skilled in the art, the now preferred method of making it is set forth:

A mixture of $Na_2CO_3$ (95 g) dissolved in $H_2O$ (1.5 L.), 5-chloroisatoic anhydride (180 g, 0.86 mole) and aminoacetaldehyde dimethyl acetal (90 g, 0.86 mole) was stirred under ambient conditions for 20 hours. The mixture was then heated to 70°–80° and stirring continued for 1.0 hour.

After cooling, the solid was collected and air dried to give 121 g (0.47 mole, 54%) of crude product. Recrystallization of 30 g (0.12 mole) from $H_2O$ gave 9.2 g (0.036 mole, 30%) of purified product. Drying at 60° C. under vacuum gave the analytical sample. Overall yield was 16%, m.p. 93.5°–95° C.

Anal. Calcd. for $C_{11}H_{15}N_2O_3Cl$: C, 51.96; H, 5.84; N, 10.83. Found: C, 51.31; H, 5.91; N, 10.81.

What is claimed is:

1. The compound 2-amino-5-chloro-N-(2,2-dimethoxyethyl)benzamide.

* * * * *